United States Patent [19]
Krepinsky et al.

[11] Patent Number: 5,416,025
[45] Date of Patent: May 16, 1995

[54] SCREENING TEST FOR EARLY DETECTION OF COLORECTAL CANCER

[76] Inventors: Jiri J. Krepinsky, 810 Srigley Street, Newmarket, Canada, L3Y 1X7; Jacek Chociej, 43 Valleywoods Rd. #89, Toronto, Canada, M3A 2R5; Gabor P. Kandel, 430 Heath St. East, Toronto, Canada, M4G 1B5; Ka Sing Yeung, 810 Srigley St., Newmarket, Canada, L3Y 1X7

[21] Appl. No.: 299,330
[22] Filed: Aug. 31, 1994

Related U.S. Application Data

[63] Continuation of Ser. No. 158,294, Nov. 29, 1993, abandoned.
[51] Int. Cl.[6] .................. G01N 33/68; G01N 33/53; C12Q 1/26
[52] U.S. Cl. ...................... 436/63; 436/64; 436/166; 436/169; 435/40.51
[58] Field of Search ............ 436/17, 18, 63, 64, 436/66, 166, 169, 164, 174, 813; 424/3, 7.1

[56] References Cited

U.S. PATENT DOCUMENTS

| | | | |
|---|---|---|---|
| 4,367,286 | 1/1983 | Saito et al. | 435/29 |
| 4,762,800 | 8/1988 | Rettig et al. | 436/548 |
| 4,857,457 | 8/1989 | Shamsuddin et al. | 435/810 X |
| 4,863,854 | 9/1989 | Mattes et al. | 435/7 |
| 4,962,187 | 10/1990 | Pant | 530/350 |
| 5,008,184 | 4/1991 | Linnane | 435/7.23 |
| 5,073,493 | 12/1991 | Yamashina | 435/240.27 |
| 5,162,202 | 11/1992 | Shamsuddin | 435/25 |

OTHER PUBLICATIONS

Robins, J. H. et al, "The Structure of Schiff Reagent Aldehyde Adducts and the Mechanism of the Schiff Reaction as Determined by Nuclear Magnetic Resonance Spectroscopy" Canadian Journal of Chemistry, vol. 58, 339–346 (1980).
Kasten, F. H. "The Chemistry of Schiff's Reagent" Int. Revs. Cytol., vol. 10, 1 (1960).
Lieberman, D. A. "Targeted Colon Cancer Screening: A Concept Whose Time Has Almost Come" American Journal of Gastroenterology, vol. 87, 1085–1093 (1992).
Eddy, D. M. "Screening for Colorectal Cancer" Annals of Internal Medicine, vol. 113, No. 5, 373–384 (1990).
Rex, D. K. et al. "Colonic Neoplasia in Asymptomatic Persons with Negative Fecal Occult Blood Tests: Influence of Age, Gender, and Family History" American Journal of Gastroenterology, vol. 88, No. 6, 825–831 (1993).
Boland, C. R. et al. "Alterations in Human Colonic Mucin Occurring with Cellular Differentiation and Malignant Transformation" Proc. Nat. Acad. Sci., vol. 79, 2051–2055 (1982).
Rinderle, S. J. et al. "Isolation and Characterization of Amaranthin, a Lectin Present in the Seeds of *Amaranthus caudatus*, That Recognizes the T–(or Cryptic T)–Antigen" Journal of Biological Chemistry, vol. 264, 16123–16131 (1989).
Sakamoto, K. et al. "Evaluation of a New Test for Colorectal Neoplasms: A Prospective Study of Asymptomatic Population" Cancer Biotherapy, vol. 8, 49–55 (1993).
Mandel, J. S. "Sensitivity, Specificity, and Positive Predictivity of the Hemoccult Test in Screening for Colorectal Cancers" Gastroenterology, vol. 97, 597–600 (1989).
Selby, J. V. "Effect of Fecal Occult Blood Testing on Mortality from Colorectal Cancer" Annals of Internal Medicine, vol. 118, 1–6 (1993).
Mandel, J. S. "Reducing Mortality from Colorectal Cancer by Screening for Fecal Occult Blood" New England Journal of Medicine, vol. 328, 1365–1371 (1993).
"Screening for Colorectal Cancer by Stool DNA Analysis" Lancet, vol. 339, 1141–1142 (1992).

*Primary Examiner*—Jeffrey R. Snay
*Attorney, Agent, or Firm*—Cushman Darby & Cushman

[57] ABSTRACT

A method for detecting the presence of neoplasia or cancer of the colon or rectum, which method comprises obtaining a sample of colorectal mucus from the rectum of a patient; treating the sample with Schiff's reagent and screening for neoplasia or cancer of the colon or rectum based upon the coloration produced in the sample by the treatment. The method is rapid, simple, inexpensive and provides a screening test for colorectal cancer which does not give a high percentage of false positive and false negative results. A screening test kit is provided.

3 Claims, 1 Drawing Sheet

U.S. Patent  May 16, 1995  5,416,025
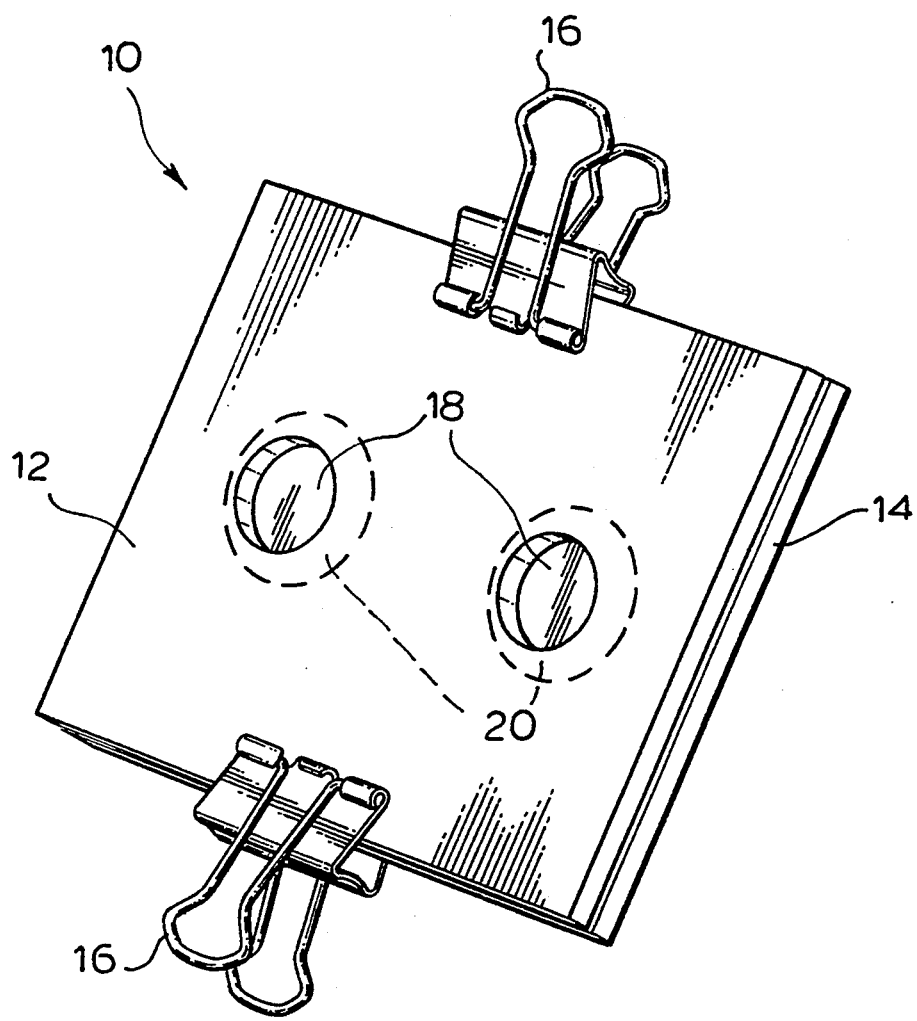
FIGURE

SCREENING TEST FOR EARLY DETECTION OF COLORECTAL CANCER

This is a continuation of application Ser. No. 08/158,294, filed on Nov. 29, 1993, which was abandoned upon the filing hereof.

FIELD OF INVENTION

This invention relates to a simple screening test for colorectal cancer. Specifically, a method is described whereby a colorectal cancer marker is detected in rectal mucus obtained by digital rectal examination. More particularly, this marker is detected in the mucus deposited on a support using Schiff's reagent.

BACKGROUND OF THE INVENTION

Colorectal carcinoma is the second most frequent cause of cancer mortality in men and women, causing nearly one third of all malignancy-related deaths in North America. It has been estimated that ultimately as many as 6% of Canadians and Americans will develop malignancy in the lower bowel, and over 50% of them will die within 5 years of diagnosis. Because there are no realistic prospects of significantly improving the cure rate once the cancer has spread beyond the bowel wall, many authorities believe that colorectal cancer can be controlled only by preventive measures (1).

Primary prevention, i.e. averting the development of the tumour by altering biological risk factors, is not yet feasible since so little is understood of the etiology of the disease. Alternatively, secondary preventive measures, i.e. detection at an asymptomatic, treatable state, would be possible should an effective screening test be available. Indeed, neoplasms of the lower bowel have the characteristics that make them a suitable candidate for the development of a screening test. This is because i) it is a common cause of cancer-related deaths, and ii) whereas once the stage of true cancer is reached, leading to symptoms, the mortality rate is over 50%, removal of bowel neoplasms at its earliest, asymptomatic stage can be done by non-surgical endoscopic polypectomy, without any significant risk. Moreover, it requires at least four to six years before an adenomatous polyp reaches the cancer stage, so there is ample opportunity to detect these neoplasms at their treatable stage. Recent clinical studies document a decrease in mortality from colorectal cancer screening, as predicted by these theoretical considerations. The problem to-date has been that polyps can be reliably detected only by endoscopy.

Thus, colorectal cancer satisfies each of the following three criteria of a disease considered suitable for a screening program. First, it is a relatively common condition with serious consequences. Second, curative treatment is available when detected at an early stage, i.e. snare polypectomy through a colonoscope or surgical segmental bowel resection. Third, the prevalence is sufficiently high to justify the expense of a screening program (2).

PRINCIPLES OF SCREENING

The goal of a medical screening program is to reduce morbidity and mortality by detecting a disease at a sufficiently early stage to allow curative treatment. It is not designed necessarily to diagnose a disease, but to determine which asymptomatic, apparently disease-free individuals should undergo diagnostic investigations. The ability of a screening test to distinguish those who warrant further evaluation from those who do not is expressed in epidemiological terms. The term "sensitivity" is defined as the proportion of diseased individuals who have a positive test, i.e. the proportion of true positives/all persons with the disease. "Specificity" is the proportion of disease-free subjects who have a negative test, i.e. the proportion of true negatives/all persons without the disease. The term "positive predictive value" is the proportion of positive tests due to the disease, i.e. the proportion of true positives/all positives. Almost always, sensitivity and specificity must be traded against each another. Intuitively, it appears wise to design a screening test for a fatal disease so as to optimize sensitivity, in order to detect as many individuals with the disease as possible. It has been emphasized, however, that optimizing sensitivity brings with it a risk of reducing specificity to such an extent that unacceptably high costs, poor compliance, and "flooding" of diagnostic facilities result. Moreover, positive predictive value, which is a particularly useful expression of the value of a screening test, is critically dependent on specificity and on the prevalence of the disease in the population screened.

It has been stressed that the effectiveness of a screening test can be properly evaluated only by randomized controlled trials. In the case of cancer, it is not sufficient to demonstrate that life is prolonged when the malignancy is detected by a positive screening test, compared to when the tumour is diagnosed after the development of symptoms. Instead, it must be shown that screened individuals have a lower death rate from the malignancy than similar individuals not enrolled in such a screening program. Important sources of error in interpreting the results of previous screening programs include lead time bias, length bias, and patient selection bias. A particularly fallacious assumption is that the predictive value of a screening test is the same in a hospitalized population with advanced disease, in which the test is usually initially tried, as it is in a healthy population with early minimal disease, to which the test is usually aimed.

CURRENT POPULATION SCREENING METHODS

Endoscopic methods, such as sigmoidoscopy or entire-length colonoscopy, are diagnostic rather than screening techniques. The only current method of colorectal cancer screening in the general population is searching for occult blood in the stool (3). Present techniques e.g. HemOccult II involve smearing a sample of stool onto guaiac impregnated paper which, after treatment with hydrogen peroxide containing developer, exhibits blue colour if blood, haemoglobin, is present. After almost two decades of experience with this methodology, it has become clear that even in expert centres, the sensitivity is less than 50% for curable neoplasms, and that the positive predictive value approximates, at best, only 40% in a clinic population. An update from the large-scale (n=97, 205) University of Minnesota, Minnesota, United States, prospective trial indicates a positive predictive value for colorectal cancer of only 2.2% when HemOccult is used in asymptomatic subjects, aged 50–80, with an overall disease prevalence of 0.2% (4). Furthermore, factors such as medications, multiple dietary constituents, delays in specimen handling, variabilities in fecal hydration, and storage of assay materials commonly confound results. Analysis of one of the three randomized controlled studies assessing the value of HemOccult suggests comparable mortality rates in the screened and control populations (5). Newer methods of detecting occult blood, e.g. methods based either on porphyrin analysis [HemoQuant] or antibody specific for human haemoglobin, may improve on these results. However, three limiting problems remain unlikely to be overcome. These are that colorectal malignancies shed blood only intermittently, upper gastrointestinal tract bleeding may make the results (falsely) positive, and multiple lesions in the lower bowel, apart from colorectal neoplasms, commonly bleed. Such lesions include hemorrhoids, diverticulae, ulcers, and vascular ectasie. Compliance in unselected populations has been estimated to be less than 30%, at least partly because the technique requires patients themselves to smear their stool onto a slide or a strip, a task most people find not only distasteful, but also technically difficult. Despite this, HemOccult continues to be widely used because the American Cancer Society has recommended occult blood testing yearly for all individuals over 50 years of age, arguing that even an imperfect test will save many lives. Implicit in all arguments over the value of HemOccult is that any improvement in screening techniques for bowel malignancy would have a dramatic impact on colorectal cancer mortality rates from the disease, since the screening for occult blood even in the present form leads to reducing mortality from colorectal cancer (6).

EXPERIMENTAL SCREENING METHODS (i) Screening for colorectal cancer by stool DNA analysis (7).

This is based on the presence in stool of neoplastic cells shed in large numbers into the colonic lumen. In principle, a mutation which is common to neoplasms could be detected with high precision by analyzing DNA from these cells. Therefore, the existence of a detectable mutation in the colorectal tumour is a prerequisite for developing such a method of screening. Unfortunately, this technique can recognize a mutation based only on a new or altered oligonucleotide sequence, but not on a loss of its portion. Thus, neoplasia-related mutations based on deletion in genes, e.g. allele losses on chromosomes such as are commonly found in colorectal tumours, are beyond the limits of the methodology. Currently, the most common mutation is the K-ras oncogene mutation present, in about 40% of colorectal carcinomas and adenomas. Screening for K-ras gene can therefore detect, at best, only 40% of all neoplasias. This methodology is at present technically very complex and expensive. (ii) Screening for the presence in colonic mucin of a cancer-related disaccharide, D-Galp($\beta$1-3)-D-GalpNAc($\alpha$1,Ser/Thr), T-(Thomsen-Friedenreich) antigen, since it is widely known that T-antigen is not expressed by cells in healthy colons, whereas it is expressed by cancer (8). (a) Monoclonal antibodies and lectins: It has been shown that monoclonal antibodies raised against synthetic T-antigen recognize and bind to cancer cells. Similarly, peanut agglutinin (PNA), a lectin, binds strongly to the same disaccharide, but recognizes malignancy with lesser specificity. Amaranthin, a lectin from *Amaranthus caudatus*, has been reported to have better specificity for T-antigen than PNA. Neither amaranthin nor PNA bind to histological sections of normal mucosa, but both bind to mucin in the goblet cells of tumours and certain polyps, and in the transitional mucosa. The visualization of the binding utilizes fluorescently labelled antibodies and lectins (9). (b) *Galactose oxidase* test. T-antigen is also reported to be detectable colorimetrically after oxidation of OH-6 of galactose using galactose oxidase and visualization of the resulting aldehyde with Schiff's reagent, - U.S. Pat. No. 4,857,457, issued Aug. 15, 1989 to Shamsuddin et al. In contrast with the tests using lectins, this test is performed on mucus samples obtained by digital rectal examination and smeared onto a support. This system demonstrated a sensitivity of 74% and specificity of 50% for colorectal neoplasms, i.e. adenomatous polyps and cancer, in one study with only 1 false negative result among 59 patients with cancer. Since then a number of reports of basically the same test have appeared with sensitivity ranging from 35% to 100% and specificity ranging from 15% to 76%. Some investigators found that the test was more sensitive, but less specific, than HemOccult. The lesser specificity has been ascribed to the positivity of test in individuals with certain inflammatory condition, such as diverticulitis and ulcerative colitis (10).

REFERENCE LIST

The present specification refers to the following publications, each of which is expressly incorporated herein by reference.

PUBLICATIONS

1. Lieberman D. A.: Targeted colon cancer screening: A concept whose time has almost come. Amer. J. Gastroenterol. 1992, 87, 1085.
2. Eddy D. M.: Screening for colorectal cancer. Ann. Int. Med. 1990, 113, 373.
3. Rex D. K., Lehman G. A., Ulbright T. M., Smith J. J., Pound D. C., Hawes R. H., Helper D. J., Wiersema M. J., Langefeld C. D., Li W.: Colonic neoplasia in asymptomatic persons with negative fecal occult blood tests: influence of age, gender, and family history. Am. J. Gastroenterol. 1993, 88, 825.
4. Mandel J. S., Bond J. H., Bradley M., Snover D. C., Church T. R., Williams S., Watt G., Schuman L. M., Ederer F., Gilbertsen V.: Sensitivity, specificity, and positive predictivity of the Hemoccult test in screening for colorectal cancer. Gastroenterol. 1989, 97, 597.
5. Selby J. V., Friedman G. D., Quesenberry, Jr. C. P., Weiss N. S.: Effect of fecal occult blood testing on mortality from colorectal cancer. Ann. Intern. Med. 1993, 118, 1.
6. Mandel J. S., Bond J. H., Church T. R., Snover D. C., Bradley G. M., Schuman L. M., Ederer F.: Reducing mortality from colorectal cancer by screening for fecal occult blood. New Engl. J. Med. 1993, 328, 1365.
7. Editorial: Screening for colorectal cancer by stool DNA analysis. Lancet 1992, 339, 1141.
8. Boland C. R. Montgomery C. K., Kim Y. S.: Alterations in human colonic mucin occurring with cellular differentiation and malignant transformation. Proc. Natl. Acad. Sci. USA 1982, 79, 2051.
9. Rinderle S. J., Goldstein I. J., Matta K. L., Ratcliffe R. M.: Isolation and characterization of Amaranthin, a lectin present in the seeds of Amaranthus caudatus, that recognizes the T- (or cryptic T) antigen. J. Biol. Chem. 1989, 264, 16123.
10. Sakamoto K., Muratani M., Ogawa T., Nagamachi Y.: Evaluation of a new test for colorectal neoplasms: a prospective study of asymptomatic population. Cancer Biotherapy 1993, 8, 49.
11. Robins J. H., Abrams, G. D., Pincock J. A.: The structure of schiff reagent aldehyde adduct and the mechanism of the Schiff reaction as determined by nuclear megnetic resonance spectroscopy. Can. J. Chem. 1980, 58, 339.

12. Kasten F. H.: The chemistry of Schiff's reagent. 1960, Int. Revs. Cyto 1.10, 1.

13. Shamsuddin A.: Diagnostic assays for colon cancer. CRC Press, Boca Raton Fla., 1991.

PATENTS

1. U.S. Pat. No. 4,857,457, Shamsuddin et al, Aug. 15, 1989.
2. U.S. Pat. No. 4,762,800, Rettig et al, Aug. 9, 1988.
3. U.S. Pat. No. 4,863,854, Mattes et al, Sep. 5, 1989.
4. U.S. Pat. No. 4,962,187, Pant, Oct. 9, 1990.
5. U.S. Pat. No. 5,073,493, Yamashina, Dec. 17, 1991.
6. U.S. Pat. No. 5,008,184, Linnane, Apr. 16, 1991.

SUMMARY OF THE INVENTION

In contrast to the above-noted prior art, we have surprisingly discovered that mucus collected from individuals with neoplastic disease of the colorectum contains a marker which produces coloration with Schiff's reagent. This assay does not require detecting the disaccharide marker beta-D-Gal(1->3)-D-GalNAc, as required by the prior art. In fact, this disaccharide does not react with the Schiff's reagent.

It is an object of the present invention to provide a tool for the screening of asymptomatic persons for cancer of the large bowel and rectum.

It is a further object of the present invention to provide a screening test to detect neoplasms of the large bowel and rectum prior to development of a bleeding cancer.

It is yet a further object of the present invention to provide a screening test for colorectal cancer which does not give a high percentage of false positive and false negative results.

It is still yet a further object of the present invention to provide a screening test kit by means of which said test can be conducted outside of a hospital, medical laboratory or clinic.

These and other objects and advantages of the invention will be seen from a reading of the specification as a whole.

Accordingly, the invention provides in one aspect a method for detecting the presence of precancer or cancer of the colon or rectum, which method comprises obtaining a sample of colorectal mucus from the rectum of a patient; treating said sample with Schiff's reagent and detecting precancer or cancer of the colon or rectum based upon the coloration produced in said sample by said treatment.

Such coloration does not develop with basic fuchsin alone, although the Schiff's reagent itself is prepared from basic fuchsin (11).

The important advantage of testing rectal mucus, compared to lectin or antibody binding to histological sections of tumour tissue, is the easy accessibility of the material to be tested. Since the luminal surface of the colon is lined throughout its length with mucus, a viscoelastic gel composed of water, electrolytes, organic chemical substances, and large molecular weight glycoproteins (mucins), as well as sloughed cells and bacteria, which is movable along the bowel, it is suggested that rectal mucus contains mucus from the entire colon, i.e., the mucus secreted by a neoplastic tissue flows along the bowel into the rectum at which point it is sampled.

A mucus sample obtained by a physician or a trained nurse from a screened subject is deposited on a suitable water-insoluble substrate or support, such as a pad or disc. Suitable support materials are, for example, glass microfibres Whatman GF/C, polymer fibres such as Biotrace RP, Metricel DM 450, Metricel VM-1, Sepraphore III, Versapore 450, or cellulose fibre such as Whatman 3MM. The support may or may not be pretreated with an antioxidant such as BHT (butylated hydroxytoluene) or BHA (butylated hydroxyanisol).

Two procedures are preferably employed.

In procedure A, the mucus sample is deposited on a support as described hereinbelow, the mucus-carrying support is rinsed in potassium phosphate buffer, generally for about 10 minutes, then water, excess water removed and the support placed in Schiff's reagent for a short period of time, such as 1 minute, washed briefly with distilled water, and dried, for example in air or by pressing it between two stacks of filter paper or both. A positive reaction is scored when a purple-magenta colour appears on the filter in 20-25 minutes.

In procedure B, the mucus sample is deposited on a support already containing Schiff's reagent, as described hereinbelow. The support develops the purple-magenta colour within a short period of time, such as 30-60 seconds after the mucus specimen is deposited, if the marker is present.

The support, such as a pad, is, for procedure B, dipped in or otherwise treated with the solution of Schiff's reagent of appropriate strength to provide an effective, suitable amount retained on the pad to effect appropriate detection by colouration of the marker.

We have observed that the mucus smeared-pad, when exposed to air for prolonged periods of time, usually at least one hour, after treatment with Schiff's reagent, becomes uniformly coloured, due to the oxidation of the Schiff's reagent. Although a true positivity is readily distinguished from such background, such background can be further minimized by antioxidant pretreatment as hereinbefore described.

If a mucus specimen does not produce any coloration, it is either because of the absence of the marker in the mucus, or because mucus was not collected by the gloved finger and therefore not deposited on the support. To distinguish between these two possibilities, the negative-testing mucus-treated support is treated with 0.5% periodic acid solution for 5 minutes, rinsed with water, stained with Schiff's reagent and rinsed again. When mucus lacking the marker is present, purple-magenta coloration appears; otherwise the support remains colourless, although some background coloration may develop.

During the practice of the process according to the invention, different shades of colour are sometimes observed. Such variations may reflect structural differences in the marker and could possibly correlate with clinical condition of the subject, e.g., chronic inflammation, ulcerative colitis, and the like.

It is known that the chemical properties of Schiff's reagent vary according to its method of preparation. Accordingly, a number of these variants were prepared and tested for use in the process of the present invention. The particulars of the various methods of preparation are listed hereinbelow. We have found that differences in colouration, sensitivity, specificity and oxidisability were obtained. While providing reasonably reproducible results, some of the Schiff's reagents listed below, for instance, were either overly sensitive, or poorly sensitive to the mucus specimen or gave a less than satisfactory background colouration. To obtain reproducible results with maximum sensitivity, the preferred Schiff's reagent No. 1 described below has been developed.

It is noted that commercial basic fuchsin (p-rosanilin) is often quite impure and Schiff's reagent is preferably prepared therefrom by purification before use. Sulphur dioxide, necessary for the preparation of the reagent, can be used as such in the gaseous form, or generated in situ from various precursors, such as $NaHSO_3$, $SOCl_2$, $K_2S_2O_5$ and $Na_2S_2O_5$,(12). We have found that the method of preparation of the Schiff's reagent determines to some degree the reactivity, sensitivity, and stability of the reagent.

In a further aspect, the invention provides a screening kit comprising a container such as a package, carton, tube, box, roll, tape, or other capsule like object comprising a water-insoluble substrate capable of absorbing colorectal mucus and Schiff's reagent.

The support (substrate) may have been pre-treated with a solution of the Schiff's reagent to retain an active portion thereof; or the container may have each of the support and the Schiff's reagent separately packaged; or the Schiff's reagent may be generated before use from basic fuchsin deposited on the support.

In a further aspect, the invention provides a screening kit as hereinabove defined but incorporating packaged basic fuchsin instead of Schiff's reagent. The basic fuchsin is provided as a source of Schiff's reagent by subsequent reaction of sulphur dioxide with the basic fuchsin.

BRIEF DESCRIPTION OF THE DRAWINGS

In order that the invention may be better understood preferred embodiments will now be described by way of example only, with reference to the accompanying drawing wherein the FIGURE shows a perspective view of an apparatus of use in the practice of the invention.

DESCRIPTION OF PREFERRED EMBODIMENTS

The FIGURE shows generally as 10, a frame assembly comprising a pair of rectanqularly-shaped plates 12 and 14 (10 cm×10 cm×3 mm) formed of Plexiglass ® thermoplastic. Upper plate 12 is operably superimposed upon lower plate 14 in firm abutment together by means of a pair of opposed clips 16.

Plate 12 has a pair of circular apertures 18 (2 cm diameter). Retained between plates 12, 14 directly below apertures 18, as to be accessible therethrough, is a pair of disc supports 20, formed of Sepraphore III polymer film (2.5 cm diameter).

In operation, a physician or nurse, for example, smears a mucus specimen onto the surface of each of pads 20, via apertures 18. Clips 16, are released and discs 20 processed as hereinbelow described, either in reference to Procedure A, or the subsequent results read directly in frame assembly 10 according to procedure B. Discs 20 are subsequently removed and discarded. Plates 12 and 14 are generally washed and re-used.

Two general procedures are hereinbelow described as a screening test for the early detection of colorectal neoplasia.

Procedure A:

A Sepraphore III support in the form of a disc, upon which a mucus specimen, obtained during the digital rectal examination, is smeared, is fastened in a frame formed by two square Plexiglass ® plates, which may be conveniently handled in a physicians office. A suitable lubricant, such as glycerol, for the rectal examination is chosen from among those that do not react with Schiff's reagent. For processing, the following method has been found to be suitable, because it minimizes background coloration.

A support bearing a smeared-on mucus specimen is placed in 0.1M potassium phosphate buffer (pH 6.5-6.7) for 10 minutes, taken out and washed briefly with distilled water. Excess water is removed by placing the support on a cellulose filter with the side bearing the mucus smear in an up position. The support is then placed in Schiff's reagent denoted No. 1 described hereinbelow, for 1 minute, taken out, washed briefly with distilled water, squeezed between two cellulose filters, and air dried. A positive reaction is scored when a purple-magenta colour appears on the filter within 20–25 minutes. Omitting the buffer wash leads to a decreased test specificity even if the sensitivity is maintained.

Stools deposited on the support together with the mucus cause an unwanted transformation in deposited mucus to take place during the storage before development, to result in a positive test reading. To prevent this transformation from happening, a pretreatment of the mucus free support is carried out before use with 0.1% solution of an antioxidant, such as, for example, BHT in 95% ethanol, or BHA.

Two mucus samples are preferably obtained from each subject, one sample is used for testing and the other used for confirmatory purposes. It should be noted that usually unequal quantities of mucus are found deposited on the supports. The specimens are then treated with the Schiff's reagent, the results are recorded, and the specimens further treated with periodic acid-Schiff's reagent to determine the quantity of mucus deposited. This procedure has shown that a weakly positive mucus-Schiff test result is to be expected if only a small amount of mucus is present on the support. This has, thus, the same validity as a strongly positive result of an abundant mucus sample.

Procedure B: A suitable support is prepared as follows: A cellulose pad or disc (Whatman 3MM) is soaked in 0.1% solution of BHT in 95% ethanol and dried. Then it is soaked in Schiff's reagent #1, and dried. This pre-treated support can be stored at −20° C., or sealed to prevent contact with air. Alternatively, the support after deposition thereon of Schiff's reagent, for additional protection, may be again soaked in BHT solution and dried.

The specimen of mucus obtained on a gloved finger after digital sampling is smeared on this support. The specimen is positive for the marker if the coloration develops within approximately up to one minute after the specimen was deposited on the support. Later colour development does not represent positivity.

Since the treatment with phosphate buffer solution is omitted in procedure B, the specificity of procedure B is lower than that of procedure A (from 80-90% to 60-70%). Since the sensitivity remains close to 100%, the negative results represent the disease-free individuals. Positive results can be reexamined by procedure A to increase specificity of the testing.

A number of Schiff's reagents of use in the invention are prepared as follows.

1. Basic fuchsin,(0.2 g) is dissolved in hot water (100 mL), boiled for 5 minutes, filtered and cooled to room temperature. Sodium bisulfite (1.17 g) and 1N hydrochloric acid (17 mL) are added sequentially to the filtrate and the solution allowed to stand in a dark place at room temp. for 4 days. Decolorizing charcoal (0.15 g) is added, mixed well, and filtered off. The resulting colourless or slightly yellow solution is stable for suitable prolonged periods of time. The reagent is stored at +4° C. in a refrigerator.

2. Basic fuchsin (1.0 g) is dissolved in hot water (200 mL), boiled for 5 minutes, filtered and cooled to room temperature. Then sodium metabisulfite (1.0 g) and 1N hydrochloric acid (20 mL) are added sequentially to the filtrate and the solution allowed to stand in a dark place at room temp. for 4 days. Charcoal (0.3 g) is added, mixed well, and filtered off.

3. Basic fuchsin (1.0 g) is dissolved in hot water (200 mL), boiled for 5 minutes, filtered and cooled to room temperature. Then potassium metabisulfite (1.0 g) and 1N hydrochloric acid (20 mL) are added sequentially to the filtrate and the solution allowed to stand in a dark place at room temp. for 4 days. Charcoal (0.3 g) is added, mixed well, and filtered off. ps 4. Basic fuchsin (1.0 g) is dissolved in hot water (200 mL), boiled for 5 minutes, filtered and cooled to room temperature. Then potassium metabisulfite (1.0 g) and 1N hydrochloric acid (25 mL) are added sequentially to the filtrate and the solution allowed to stand in a dark place at room temp. overnight. If the solution is still coloured, two drops of 6N hydrochloric acid are added, stored in a dark place for 48 hours. Then charcoal is added, mixed well, and filtered off.

5. Basic fuchsin (0.2 g) is dissolved in hot water (100 mL), boiled for 5 minutes, filtered and cooled to room temperature. After thionyl chloride (7-8 mL) is added to the filtrate, the solution is allowed to stand in a dark place at room temp. for 24 hours. Charcoal is added to decolorize the solution, mixed well, and filtered off.

6. Basic fuchsin (1.0 g) is dissolved in 0.25 M hydrochloric acid (100 mL) and sodium bisulfite (10.0 g) is added. The solution has pH=3. ps Basic fuchsin (0.12 g) is dissolved in hot water (200 mL), boiled for 5 minutes, filtered and cooled to room temperature. Then glacial acetic acid (11.40 mL) and sodium bisulfite (1.0 g) are added sequentially to the filtrate. The solution is slightly pink in colour.

8. Commercial Schiff's reagent (Fischer) pH=1 is adjusted to pH=3 by the addition of aqueous sodium hydroxide (0.2 N). The resultant pink solution is decolorized with sodium bisulfite.

9. Basic fuchsin (1.0 g) is dissolved in hot water (200 mL), boiled for 5 minutes, filtered and cooled to room temperature, Then sodium bisulfite (1.0 g) and 1N hydrochloric acid (25 mL) are added sequentially to the filtrate and the solution allowed to stand in a dark place at room temp. for 48 hours. Charcoal (0.3 g) is added, mixed well, and filtered off.

10. Basic fuchsin (1.0 g) is dissolved in hot water (200 mL), boiled for 5 minutes, filtered and cooled to room temperature. Then sodium bisulfite (2.0 g) and 1N hydrochloric acid (25 mL) are added sequentially to the filtrate and the solution allowed to stand in a dark place at room temp. for 48 hours. Charcoal (0.3 g) is added, mixed well, and filtered off.

11. To commercial Schiff's reagents (Sigma) pH=1.5 (100 mL) is added glacial acetic acid (4.5 mL).

EXAMPLES

EXAMPLE 1

In all investigated groups, using modified procedure A, clinically diagnosed cancers were detected with high sensitivity, minimum 92%. In one study, out of 25 cancer patients, 23 gave a positive result in the mucus-Schiff test; of 30 large adenomatous polyps, 24 gave positives; of 76 small polyps, 43 gave positives.

It has been shown by the results in this group that colonic inflammatory conditions such as ulcerative colitis, diverticulitis, Crohn's disease, acute and chronic inflammation often give positive results (Table). Since at least some of these conditions have been recognized as risk factors for colorectal cancer, these results show that the test recognizes either susceptible individuals or an early stage of neoplastic development. The latter argument applies to polyps as well.

EXAMPLE 2

A study was designed to compare patients visiting the endoscopy unit with patients visiting physicians' (gastroenterologists') offices for non-malignant disease. The visits were due to unspecified complaints. The latter group consisted of 45 patients and the former of 39 patients. Two specimens were prepared from each patient. Modified procedure A was used. The two main differences between the groups were: (a) the endoscopy suite group received colonic lavage beforehand to free the colon of faeces, and was on a liquid diet for 24 hours prior to the mucus collection (and colonoscopy), while (b) the other group did not receive lavage and had no diet restrictions.

The results show positivity of 27% (95% confidence interval: 15.4–42.6), 12/45 among patients in physicians' offices and 33% (95% confidence interval: 19.3–48.4), 13/39 among patients in the endoscopy suite. This study thus shows that the presence of faeces in specimens, and normal food intake, do not determine the percentage of the positivity. The positivity is consequently due to a condition other than colorectal cancer.

EXAMPLE 3

The specificity measured in clinical control populations is very imprecise in patients, who at the moment of the test, have no clinically detected neoplasms but have some other unspecified ailments, which may well predispose to cancer formation in the future. Thus, a study was designed to determine the number of positives in a cohort of 47 young adult volunteers unlikely to suffer of any intestinal ailment or neoplastic condition. All individuals were between 18 to 35 years of age and feeling completely healthy. This investigation was expected to provide an estimate of specificity of the investigated screening tool. Four specimens were collected from each individual.

The results described in Examples 2 and 3 suggest that some individuals may have a condition increasing the risk of neoplasia. The false positive rate among healthy young volunteers (not patients) was found to be low (10.6%). A segment of inflamed bowel may, in fact, be transformed into a preneoplastic condition, and this perhaps is detected by the test.

The high sensitivity and relatively high specificity of the test for neoplasms may reduce the number of patients undergoing colonoscopy because they have rectal bleeding, unexplained iron-deficiency anemia, or a first-degree relative with a tumour.

The Table shows the results of Schiff's reagent analysis of mucus from a group of patients with colorectal cancer and putative precancerous conditions at the endoscopy unit at the Wellesley Hospital, Toronto, Ontario, Canada, who agreed to submit themselves to the mucus testing.

The following notes provide a better understanding of the Table:

(a) The two cancer patients listed as negative had an ambiguous reation due to very small amount of mucus deposited on pads. They underwent surgery before the test could be repeated;

(b) The positivity/negativity of polyps reflects the well-known observation that some polyps are cancer precursors whereas some are not;

(c) Laser treatment probably inhibits mucus production by tumour, especially if the laser coagulation is extensive;

TABLE

| Diagnosis | total # of cases | positive # | % | 95% CI** | negative # | % |
|---|---|---|---|---|---|---|
| Cancer | 25 | 23 | 92 | 72.5–98.6 | 2 | 8 |
| Polyp adenomatous (<1 cm in diameter) | 76 | 43 | 57 | 45.1–68.1 | 33 | 43 |
| Polyp adenomatous (<1 cm in diameter; removed endoscopically 2–8 weeks prior to mucus collection) | 5 | 3 | | | 2 | |
| Polyp adenomatous (<cm in diameter) | 30 | 24 | 80 | 59.7–91.6 | 6 | 20 |
| Carcinoma (laser treated) | 6 | 1 | | | 5 | |
| Carcinoma (removed 2–8 weeks before mucus collection) | 7 | 5 | | | 2 | |
| Ulcerative colitis | 6 | 4 | | | 2 | |
| Crohn's disease | 7 | 3 | | | 4 | |
| Diverticulitus | 1 | 1 | | | | |
| Acute inflammation | 2 | 2 | | | | |
| Chronic inflammation | 1 | 1 | | | | |

TABLE-continued

| Diagnosis | total # of cases | positive # | % | 95% CI** | negative # | % |
|---|---|---|---|---|---|---|
| Acute colitis | 1 | | | | 1 | |
| TOTAL | 167 | | | | | |

(d) Positivity/negativity of the test in previously removed carcinomas may reflect the completeness of the cancer removal;

(e) Inflammatory conditions are considered a risk factor for colonic cancer. The positivity in the test may reflect how far an inflammation has progressed to an early stage of cancer development;

(f) *Percentage of groups with less than 10 subjects are not calculated; and (g) **CI, Confidence Interval of percentage positive.

Although this disclosure has described and illustrated certain preferred embodiments of the invention, it is to be understood that the invention is not restricted to those particular embodiments. Rather, the invention includes all embodiments which are functional or mechanical equivalents of the specific embodiments and features that have been described and illustrated.

We claim:

1. A method for detecting the presence of neoplasia or cancer of the colon or rectum, which method consists essentially of obtaining a sample of colorectal mucus from the rectum of a patient; treating said sample, without a step of adding an enzyme for detecting the disaccharide marker beta-D-Gal (1->3)-D-GalNAc, with Schiff's reagent; and detecting neoplasia or cancer of the colon or rectum based upon the coloration produced in said sample by said treatment.

2. A process as claimed in claim 1 wherein said mucus is absorbed onto a water-insoluble substrate.

3. A process as claimed in claim 2 wherein said water-insoluble substrate has been pre-treated with an antioxidant.

* * * * *